United States Patent
Bylsma et al.

(10) Patent No.: US 8,224,481 B2
(45) Date of Patent: Jul. 17, 2012

(54) METHOD AND APPARATUS FOR DISPENSING FLUID COMPOSITIONS

(75) Inventors: Richard B. Bylsma, Ada, MI (US); David W. Baarman, Fennville, MI (US); Mark G. Marshall, Cape Town (ZA); Pierre Becker, Cape Town (ZA)

(73) Assignee: Access Business Group International LLC, Ada, MI (US)

( * ) Notice: Subject to any disclaimer, the term of this patent is extended or adjusted under 35 U.S.C. 154(b) by 709 days.

(21) Appl. No.: 12/355,874

(22) Filed: Jan. 19, 2009

(65) Prior Publication Data
US 2010/0185322 A1 Jul. 22, 2010

(51) Int. Cl.
*G06F 17/00* (2006.01)
(52) U.S. Cl. .................. 700/239; 222/145.5; 222/129.4; 222/134
(58) Field of Classification Search .................. 700/239; 222/129.4, 134, 135, 145.5, 145.6
See application file for complete search history.

(56) References Cited

U.S. PATENT DOCUMENTS

| | | | |
|---|---|---|---|
| 3,633,420 A * | 1/1972 | Holzem | 73/199 |
| 3,683,790 A | 8/1972 | Black et al. | |
| 3,747,892 A | 7/1973 | Gigantino et al. | |
| 3,776,423 A | 12/1973 | Phillips | |
| 4,150,767 A | 4/1979 | Pitches et al. | |
| 4,331,262 A | 5/1982 | Snyder et al. | |
| 4,473,173 A | 9/1984 | DeGroff et al. | |
| 4,705,083 A | 11/1987 | Rossetti | |
| 4,790,454 A | 12/1988 | Clark et al. | |
| 4,809,909 A | 3/1989 | Kukesh | |
| 4,854,721 A | 8/1989 | Hume | |
| 5,131,420 A | 7/1992 | Favret et al. | |
| 5,545,968 A | 8/1996 | Hilfinger et al. | |
| 5,697,527 A * | 12/1997 | Altieri et al. | 222/132 |
| 5,794,822 A | 8/1998 | Foster | |
| 5,903,465 A | 5/1999 | Brown | |
| 5,950,448 A | 9/1999 | Barnes et al. | |
| 6,050,282 A * | 4/2000 | Whaley | 137/3 |
| 6,540,100 B2 * | 4/2003 | Credle et al. | 221/2 |

(Continued)

FOREIGN PATENT DOCUMENTS

DE 202008001224 4/2008

(Continued)

OTHER PUBLICATIONS

International Search Report, International Application No. PCT/US2009/059919, Mar. 4, 2010.

(Continued)

*Primary Examiner* — Timothy Waggoner
(74) *Attorney, Agent, or Firm* — Warner Norcross & Judd LLP

(57) ABSTRACT

A miniaturized fluid dispensing system for dispensing customized fluids. The dispenser may include first and second reservoirs containing constituent fluids; a drive motor; at least two pump assemblies commonly driven by the drive motor and in communication with the first and second reservoirs; first and second valve assembly in communication with the first and second pump assemblies; and a control system for selectively controlling the valve assemblies to blend and discharge a composition from the constituent fluids. The system may include a dispensing header to house the valves and to define 'discharge' and 'recirculation' flow paths for each constituent fluid. The present invention also provides a method for dispensing a fluid regimen (e.g. a plurality of compositions) by periodically blending and discharging varying compositions over time.

24 Claims, 15 Drawing Sheets

U.S. PATENT DOCUMENTS

| | | | |
|---|---|---|---|
| 6,540,832 B2 * | 4/2003 | Cavallaro | 118/314 |
| 6,622,064 B2 * | 9/2003 | Bartholomew et al. | 700/239 |
| 6,715,642 B2 | 4/2004 | Engel et al. | |
| 6,735,468 B2 * | 5/2004 | Treppo et al. | 600/547 |
| 6,856,861 B2 | 2/2005 | Dirksing et al. | |
| 6,886,534 B2 | 5/2005 | Rodriguez-Amaya et al. | |
| 6,986,442 B2 | 1/2006 | Engel et al. | |
| 7,011,076 B1 | 3/2006 | Weldon et al. | |
| 7,131,279 B2 | 11/2006 | Kateman et al. | |
| 7,296,922 B2 | 11/2007 | Dyhr | |
| 7,320,456 B2 | 1/2008 | Yajima | |
| 7,851,775 B2 * | 12/2010 | Hoyt et al. | 250/577 |
| 2003/0202887 A1 | 10/2003 | Apostolides et al. | |
| 2006/0076080 A1 * | 4/2006 | Salas | 141/104 |
| 2007/0000947 A1 | 1/2007 | Lewis et al. | |
| 2007/0090296 A1 | 4/2007 | Hoyt et al. | |
| 2007/0110872 A1 | 5/2007 | Gerber | |
| 2007/0119311 A1 | 5/2007 | Beretta | |

FOREIGN PATENT DOCUMENTS

| | | |
|---|---|---|
| EP | 0243677 | 11/1987 |
| EP | 0283137 | 9/1988 |
| EP | 0299781 | 1/1989 |
| EP | 0654300 | 5/1995 |
| EP | 0810398 | 12/1997 |
| EP | 0918678 | 6/1999 |
| EP | 1270502 | 1/2003 |
| GB | 1272258 | 10/1969 |
| GB | 1272258 | 4/1972 |
| GB | 2094574 | 9/1982 |
| JP | 61042326 | 2/1986 |
| JP | 63143930 | 6/1988 |
| WO | 9301123 | 1/1993 |
| WO | 9526316 | 10/1995 |
| WO | 0024522 | 5/2000 |
| WO | 0205968 | 1/2002 |
| WO | 02073142 | 9/2002 |
| WO | 02094423 | 11/2002 |
| WO | 2005115528 | 12/2005 |
| WO | 2006044585 | 4/2006 |
| WO | 2007041949 | 4/2007 |
| WO | 2007065566 | 6/2007 |
| WO | 2008029477 | 3/2008 |

OTHER PUBLICATIONS

Written Opinion of the International Searching Authority, International Application No. PCT/US2009/059919, International Filing Date Oct. 8, 2009.

"Built-In Valves for Hydraulic Pumps and Motors", Announcement Casappa, Casappa, Parma, IT, Jan. 1, 2005, pp. 1, 3-7, XP001223966, p. 17.

Supplemental International Search Report, International Application No. PCT/US2009/059919, International Filing Date Aug. 10, 2009.

Supplemental Written Opinion, International Application No. PCT/US2009/059919, International Filing Date Aug. 10, 2009.

* cited by examiner

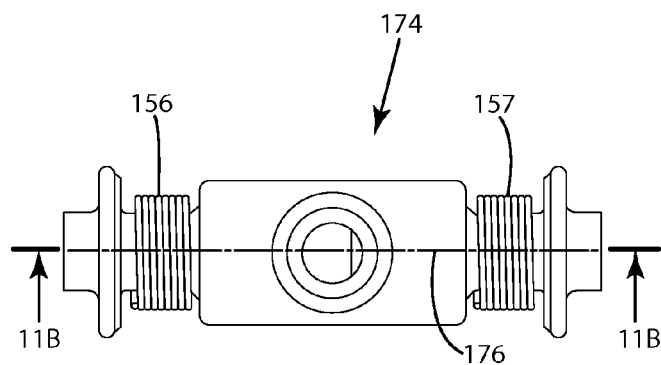
Fig. 11A
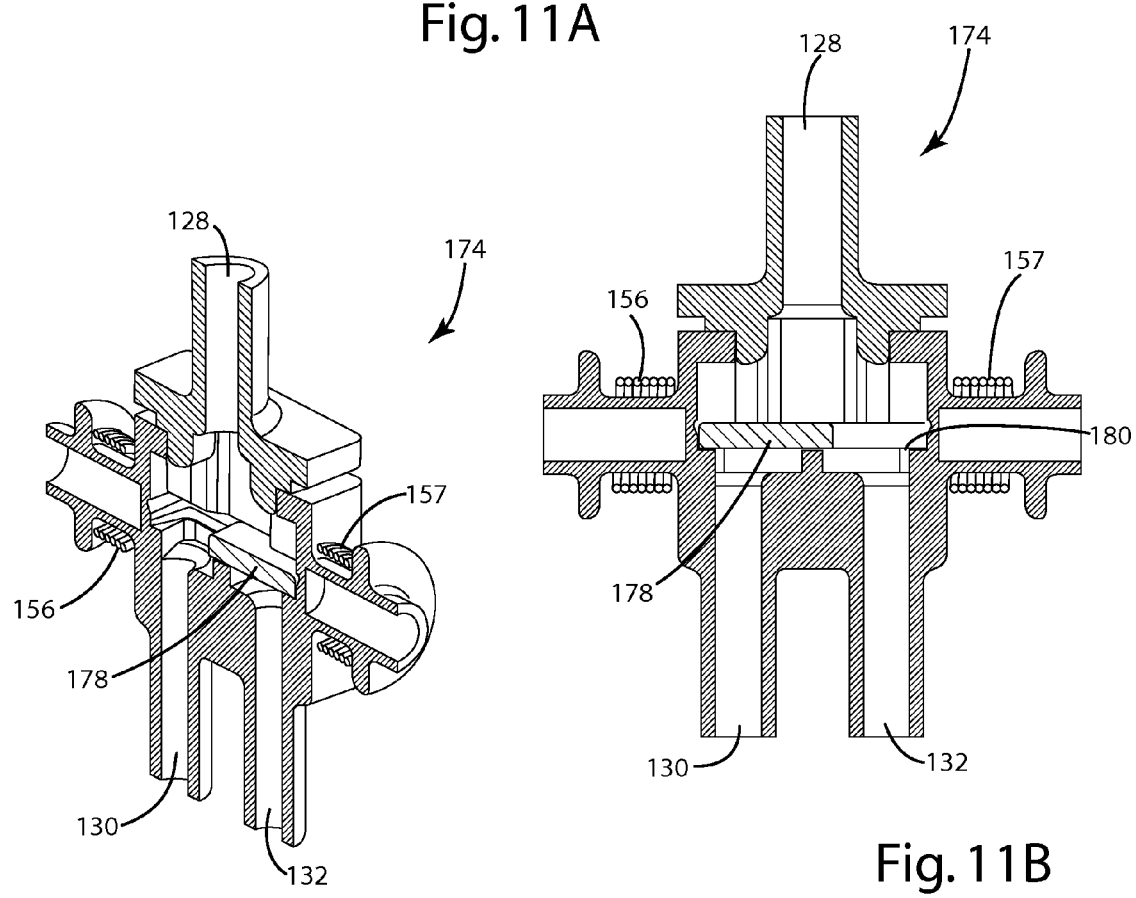
Fig. 11C
Fig. 11B

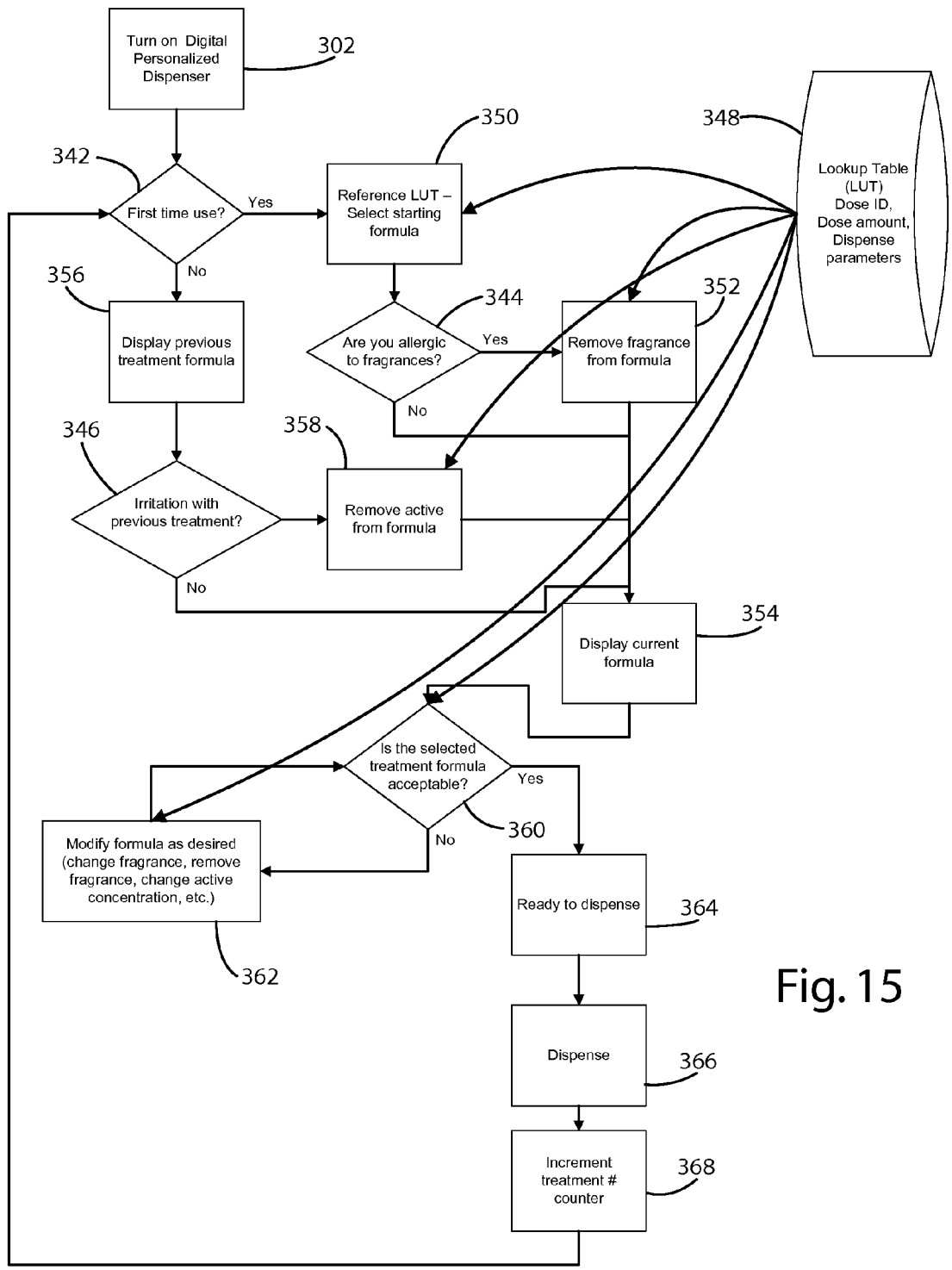

METHOD AND APPARATUS FOR DISPENSING FLUID COMPOSITIONS

BACKGROUND OF THE INVENTION

The present invention relates to fluid distribution systems, and more particularly to portable systems for dispensing fluid compositions.

Various fluid dispensers and methods for mixing and metering small quantities of fluid are well known in the prior art. Generally, fluid dispensers and associated methods have included a first stage for storing two or more fluids, a second stage for selectively mixing the fluids, and a third stage for dispensing a product containing the fluids in desired proportions. In miniaturized or portable applications, fluid dispensers have included replaceable fluid reservoirs and a small, internal energy supply for powering the miniaturized device. An example of a miniaturized fluid dispensing system is disclosed in U.S. Pat. No. 5,709,317 to Bertram et al.

In certain applications, for example the use of cosmetic products, there remains a significant and increasing interest in improved miniaturized dispenser systems, particularly miniaturized systems for generating a customized product. Historically, the cosmetics industry has offered numerous shades of colored fluid to suit a user's preferences. For example, a cosmetic such as lip-gloss, tinted cream, foundation and nail polish can be available in a broad choice of colors, including tones, shades or hues. However, even as the number of available choices has increased, the user's choice is limited by the availability of pre-manufactured mixtures. Additionally, in cosmetic or medical applications, a user may desire a product having varying compositions of a given ingredient over multiple uses. For example, as part of a prescriptive regimen, a user may desire a topical application having progressively increased dosages of active ingredient. Alternatively, a user may desire a customized topical application having decreased dosages of compounds known to induce skin irritation or allergic reactions.

Systems for dispensing customized fluids, including cosmetics and medicines, have been known for many years. However, many conventional fluid distribution systems include a variety of limitations that impede use in customized and miniaturized applications. For example, manually operated positive displacement pumps do not dispense product with the degree of precision required to generate customized fluids of the desired tone, shade or hue. An example of a multi-chambered manual dispenser is disclosed in U.S. Pat. No. 5,848,732 to Brugger. Additionally, electro-mechanically operated dispensers often require multiple motors for operation of valve and pump assemblies, often comprising a dispenser that cannot be conveniently stored in a purse or handbag. An example of an electro-mechanically operated dispenser is disclosed in U.S. Pat. No. 6,516,245 to Dirksing et al.

Therefore, there remains a need for an improved miniaturized dispenser for fluid compositions that are blended or mixed from various constituent fluids, such as fluid cosmetics or medicinal compositions. There also remains a need to provide a miniaturized dispenser that dispenses doses of customized product that vary in composition over time, including a dispenser responsive to user-supplied data and preferences.

SUMMARY OF THE INVENTION

The present invention provides a miniaturized fluid composition dispenser capable of accurately combining a plurality of constituent fluids. The dispenser generally includes a plurality of fluid reservoirs containing a plurality of different constituent fluids, a plurality of pumps for moving fluids through the dispenser, a motor for driving the pumps, a valve assembly for recirculating or discharging fluid from the fluid reservoirs to an outlet and a control system for controlling the constituents of a dispensed fluid composition.

In one embodiment, the valve assembly generally includes, for a given constituent fluid, an outlet passage, a recirculation passage and a valve for directing fluid through either the outlet passage or the recirculation passage. The outlet passage routes fluid to the outlet when desired in the dispensed composition, and the recirculation passage returns fluid to the fluid reservoir when that particular fluid is not desired. In use, the control system operates the valves to control the content of the dispensed fluid composition.

In one embodiment, the valves may be actuated electromagnetically. For example, in one embodiment, the valve may include a magnetic moving member that is moved between outlet and recirculation positions through the selective application of electromagnetic fields. The valve may include a pair of electromagnetic coils disposed on opposite sides of the moving member. In use, power may be selectively applied to the coils to actuate the moving member. The coils may be configured with opposite polarity such that they operate in a push/pull arrangement. Using cooperative action, the overall size of the coils required to operate the moving member is reduced.

In one embodiment, the dispenser includes a single motor that provides motive force for all of the pumps. In this embodiment, the pumps for all fluids may be driven together, for example, using a single transmission. In one embodiment, the motor drives a worm gear, which in turn drives a plurality of gear pumps.

In one embodiment, the motor is an electric motor and the system includes a charge storage device, such as a battery, for powering the motor. The charge storage device may be rechargeable. In one embodiment, the system may include a wireless power supply that permits the battery to be recharged without direct electrical contact. The wireless power supply may also be capable of transmitting data communications with outside devices, for example, to communicate status, composition formulations and other information.

In one embodiment, the control system includes a microprocessor for managing the dispensed fluid composition according to user preferences. In operation, a user might desire a mixture composition that varies over multiple uses. For example, a given prescriptive regimen may require a user to apply a topical fluid with varying dosages of active ingredient over the course of treatment. To achieve fluids of varying compositions, the control system can manipulate the dispenser pumps and valve assemblies according to the desired dispensed fluid composition.

These and other features and advantages of the present invention will become apparent from the following description of the invention, when view in accordance with the accompanying drawings and appended claims.

BRIEF DESCRIPTION OF THE DRAWINGS

FIGS. 11A-C are various illustrations of a gate valve in accordance with an embodiment of the present invention.

FIG. 15 is a flowchart showing the general steps of a method of operation for customizing an anti-aging treatment in accordance with an embodiment of the present invention.

DETAILED DESCRIPTION OF THE CURRENT EMBODIMENT

Figures 1A, 1B:
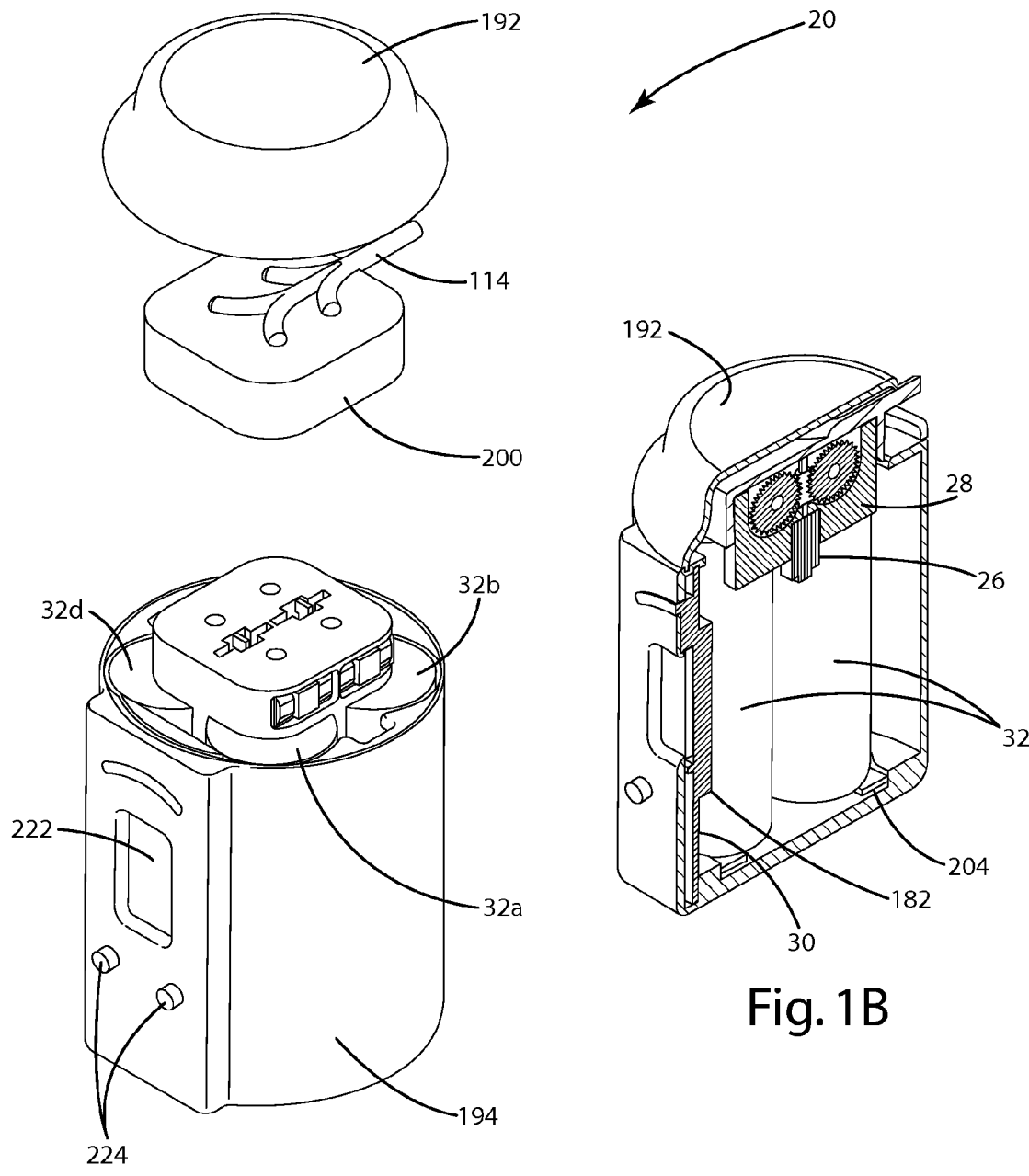
FIG. 1A is an exploded representational perspective view of an embodiment of the present invention.
FIG. 1B is a section view of the fluid dispenser in FIG. 1A.

A fluid composition dispenser 20 in accordance with an embodiment of the present invention is shown in FIG. 1A. The embodiment shown in FIG. 1A is adapted for use as a handheld dispenser ideal for cosmetic and skin care fluid compositions. The dispenser 20 may be used to generate medical, cosmetic or nutritional fluids for topical or systemic application and having varying compositions over the course of a treatment regimen. Additionally, the dispenser 20 may be used to generate personalized fluid compositions of a desired formula based on user-supplied input, including known allergies and prior skin reactions. The present invention is, however, well suited for use in other applications where miniaturized fluid blending and dispensing is desired. For example, the fluid dispenser 20 may also be used to combine vitamins, supplements and flavors in water to create a consumable beverage or food supplement.

The fluid dispenser of FIG. 1A generally includes a plurality of fluid reservoirs 32a-d, a plurality of pumps 24a-d, a single motor 26, a manifold 28 and a control system 30. The illustrated dispenser 20 includes four fluid reservoirs 32a-d intended to store a supply of up to four different constituent fluids that can be combined in various proportions to provide custom fluid compositions. Although the fluid reservoirs 32a-d may include different constituent fluids, it may be desirable in some applications for two or more of the reservoirs 32a-d to contain the same fluids.

Figure 2:
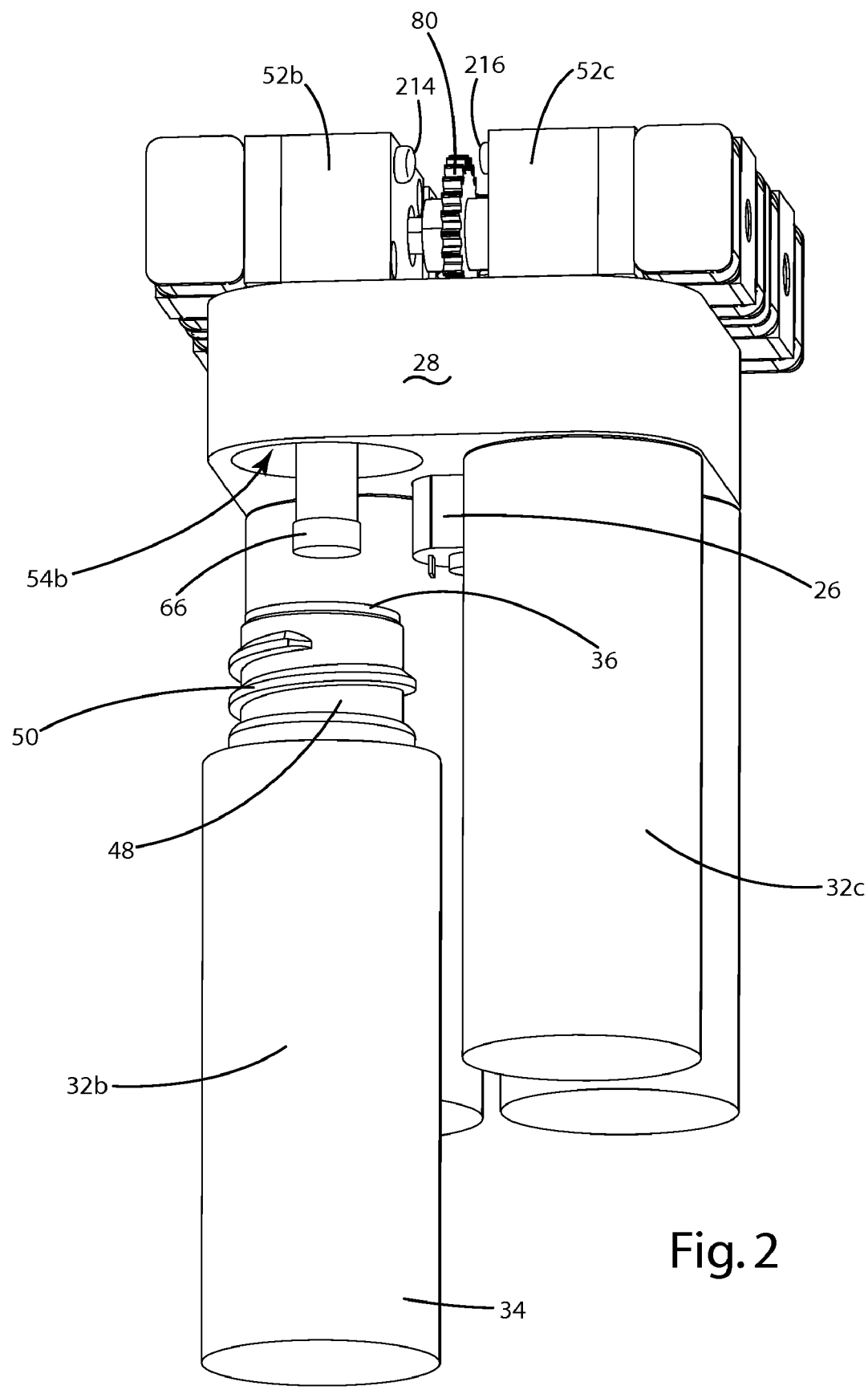
FIG. 2 is a side view of another embodiment of the present invention illustrating the fluid reservoirs in relation to the manifold.

The fluid reservoirs 32a-d may be of any desired shape capable of holding a constituent fluid. The fluid reservoirs 32a-d could contain fluids under positive pressure for assisting in dispensing fluid from the reservoir, such as by means of a spring (not shown) or conventional positive biasing mechanism. Optionally, the fluids reservoirs 32a-d may be flexible housings that collapse as fluid is withdrawn. In the current embodiment as depicted in FIG. 2, the fluid reservoirs 32a-d generally include a rigid housing 34 and an outlet 36. The fluid reservoir 32b includes a first external screw thread 50 disposed about the neck 48 and configured to mate with a portion of the manifold 28 for routing fluid to a pump housing 52b. The manifold 28 includes bosses 54a-d for receipt of a fluid reservoir neck 48, and each boss 54 includes a second external screw thread (not shown) disposed thereon and configured to engage the first external screw thread 50. The manifold 28 may alternatively include essentially any mechanism capable of securing fluid reservoirs 32a-d to the manifold 28, including, for example, a bayonet fitting or friction fitting.

Figure 3:
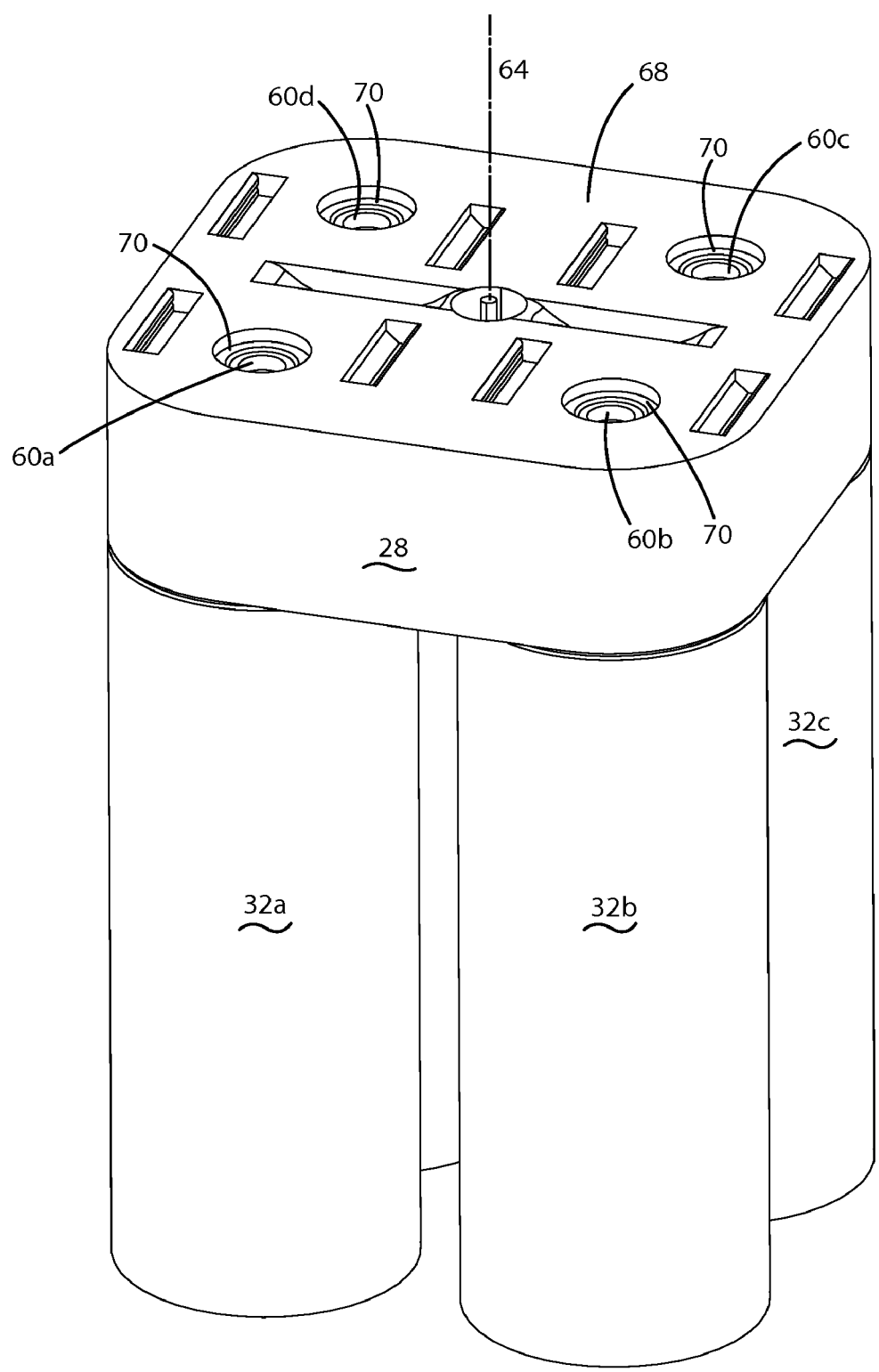
FIG. 3 is a perspective view of the fluid dispenser of FIG. 2 illustrating the manifold and fluid reservoirs.

As depicted in FIG. 3, the manifold 28 further includes apertures 60a-d for allowing communication between the fluid reservoirs 32a-b and the overlying pump housings 52a-d. The apertures 60a-d can define an aperture diameter, where the aperture diameter is less than the boss diameter. Optionally, the aperture 60 and the boss 54 share a common central axis. In the illustrated embodiment, the manifold 28 includes four identical apertures 60a-d equidistant from the central vertical axis 64 of the manifold 28. Though not shown, the manifold 28 can include any number of apertures 60 in a variety of orientations for fluid communication between a corresponding number of fluid reservoirs 32 and pump housings 52. Additionally, as depicted in FIG. 2, a dip tube 66 joined to the aperture 60 extends into the fluid reservoir 32 when the fluid reservoir 32 is joined to the manifold 28. The fluid within the fluid reservoir 32 is allowed to enter the dip tube 66, which guides the fluid vertically through the aperture 60 and into a pump housing 52. Re-circulated fluid is also allowed to enter the dip tube 66 from the pump housing 52 and transfer toward the fluid reservoir 32.

The manifold 28 can be manufactured from a rigid dimensionally stable material, such as aluminum, brass, a rigid polymer or other similar material. The dimensional stability of the manifold can ensure that each boss 54 and aperture 60 remain a predetermined size to facilitate the transfer of fluid between the fluid reservoir 32 and the overlying pump housing 52. Additionally, the upper portion 68 of the manifold 28 can include an annular recess 70 disposed around the aperture 60 to allow placement of an elastomeric o-ring (not shown). The o-ring can include an axial dimension greater than the depth of the annular recess 70 to project upward from the recess 70. Accordingly, the o-ring will be compressed in the recess 70 upon being engaged by the confronting portion of the overlying pump housing 52 to provide a seal between the manifold 28 and the pump housing 52.

Figure 4:
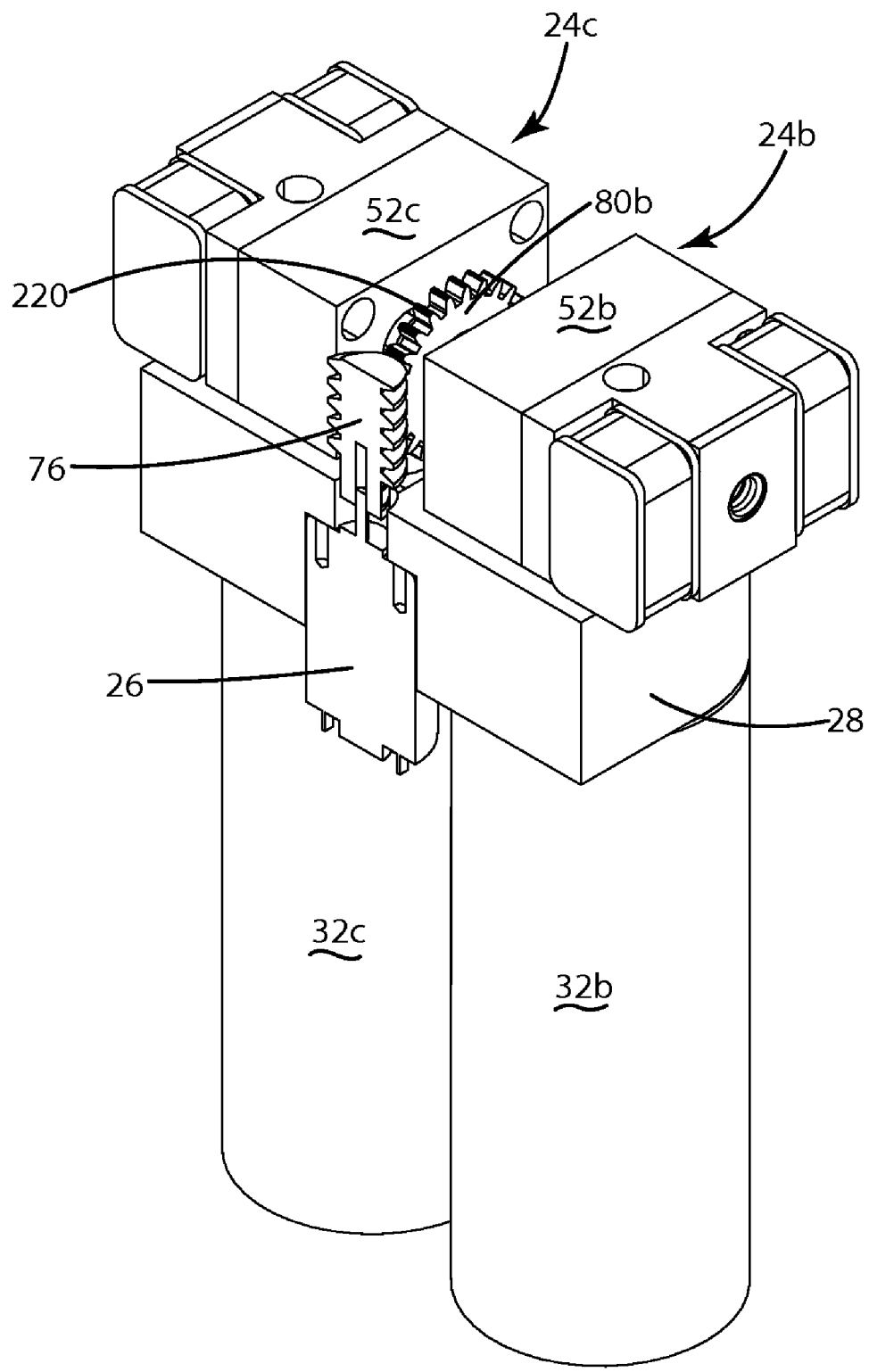
FIG. 4 is a section view of the fluid dispenser of FIG. 2.
Figure 5:
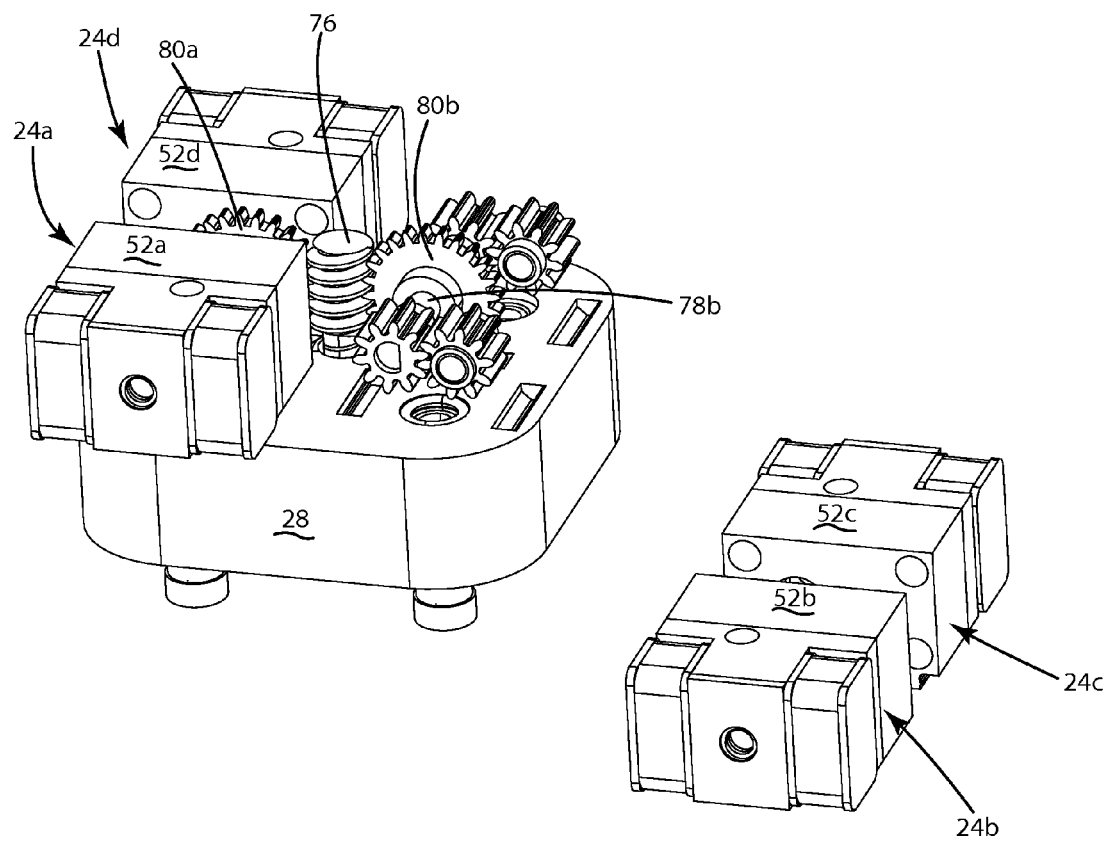
FIG. 5 is a partially exploded representational view of the fluid dispenser of FIG. 2 illustrating the transmission.

As depicted in FIG. 4, the fluid dispenser 20 further includes a motor 26 secured within at least a portion of the manifold 28. A single motor 26 is provided to drive four pumps 24a-d secured within four pump housings 52a-d, corresponding to the number of fluid reservoirs 32a-d. The motor 26 in the illustrated embodiment is a DC motor, although a stepper motor may also be used. The motor 26 is coupled to all of the pumps 24a-d by a transmission 74. In driving the illustrated embodiment as depicted in FIG. 5, the motor 26 includes a worm gear 76 that is coupled to two drive shafts 78a-b by two drive gears 80a-b. In this embodiment, the transmission 74 is a direct, fixed transmission meaning that when the motor 26 operates, all four pumps 24a-d are directly driven. As a result, when the motor 26 operates, all four pumps 24a-d move fluid.

The worm gear 76 includes an axis of rotation coaxial with the central vertical axis 64 of the manifold 28. The drive shaft 78b rotatably supports the drive gear 80b and extends along an axis perpendicular to the central vertical axis 62 of the manifold 28 between laterally opposed pump housings 52b-c. The drive shaft 78b can be journal along a portion thereof within each laterally opposed pump housing 52b-c. The drive gear 80b can be integral with the drive shaft 78b or secured thereon to prevent relative radial movement, such as by means of a key and associated keyway, and to prevent relative axial movement, such as by means of opposing pins or bushings (not shown). In operation, the motor 26 is rotated in a first direction to promote rotation of the drive shaft 78b in a corresponding first direction via the radially responsive worm gear 76 and drive gear 80b. The motor 26 can also rotate in a second direction, which via a radially responsive worm gear 76 and drive gear 80b promotes rotation of the drive shaft 78b in a corresponding second direction. Additionally, while a single motor 26 is shown as operating multiple pumps 24a-d, the dispenser may include two or more motors 26 for operating multiple pumps 24.

Figure 6:
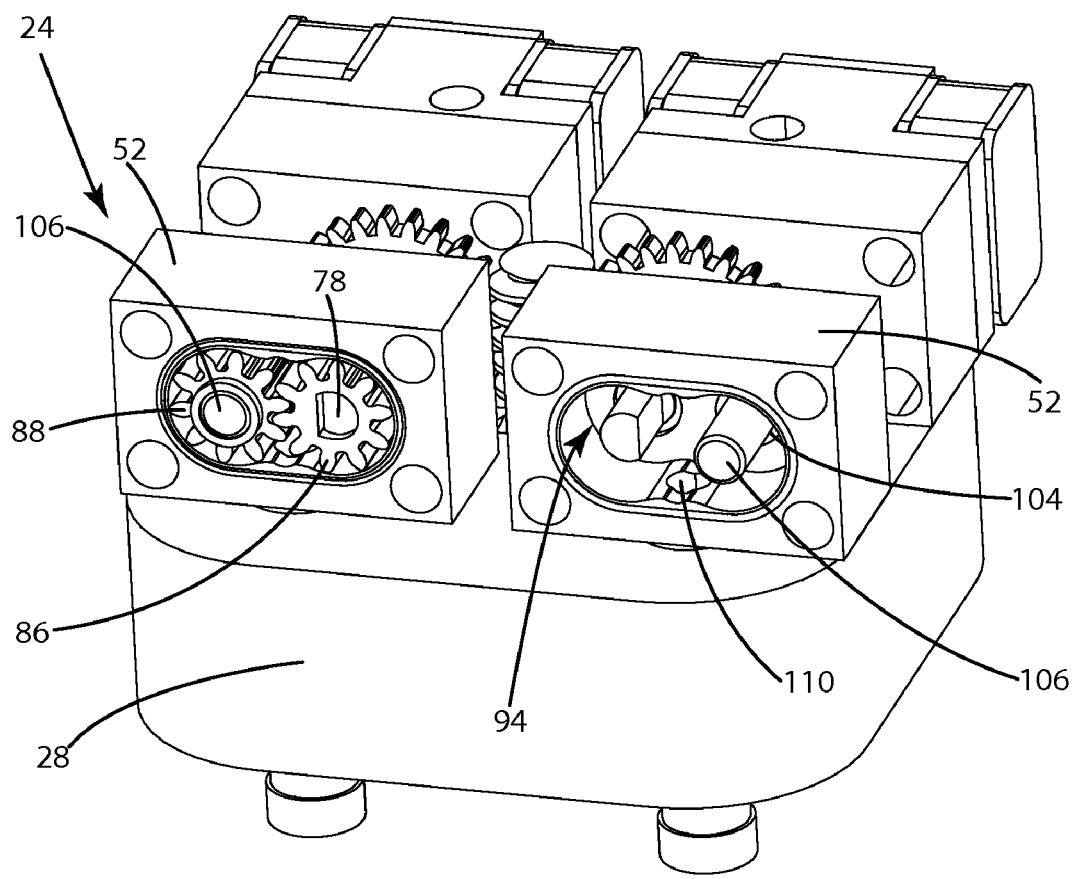
FIG. 6 is a partially exploded representational view of the fluid dispenser of FIG. 2 illustrating the pump housing.

As illustrated in FIG. 6, each pump 24 can include intermeshed gears 86, 88 driven by the drive shaft 78 to draw a fluid into the pump housing 52. A tooth drive gear 86, in operable engagement with a tooth non-drive gear 88, is fixedly mounted about a portion of the drive shaft 78 such that the tooth drive gear 86 includes an axis of rotation coaxial with the drive shaft 78 axis of rotation. The drive shaft 78 is keyed to prevent relative radial movement between the tooth drive gear 86 and the drive shaft 78. The drive shaft 78 may optionally include a splined end or other coupling mechanism to prevent relative radial movement between the tooth gear 86 and the drive shaft 78. The pump housing 52 also includes a boss 104 for receiving an idler shaft 106 therein. The tooth non-drive gear 88 is secured about a portion of the idler shaft 106 to permit radial movement of the non-drive gear 88. Additionally, the pump housing 52 defines a through hole 110 in alignment with the manifold aperture 60 to allow fluid communication between the pump chamber 94 and the dip tube 66 when the pump housing 52 is secured to the manifold 28 in operable configuration. As also shown in FIG. 6, the pump chamber 94 is configured to simultaneously accommodate the tooth drive gear 86 and the tooth non-drive gear 88, generally forming an elongated oval recess. The pump housing 52 can be machined or can be formed using conventional mold forming techniques, and the pump housing 52 may be manufactured from a dimensionally stable material, such as aluminum, brass, a rigid polymer or other similar material. The pump housing 52 can include any fastening mechanism capable of securing the fluid reservoirs to the manifold 28, including, for example, a bayonet fitting or friction fitting.

Figure 13:
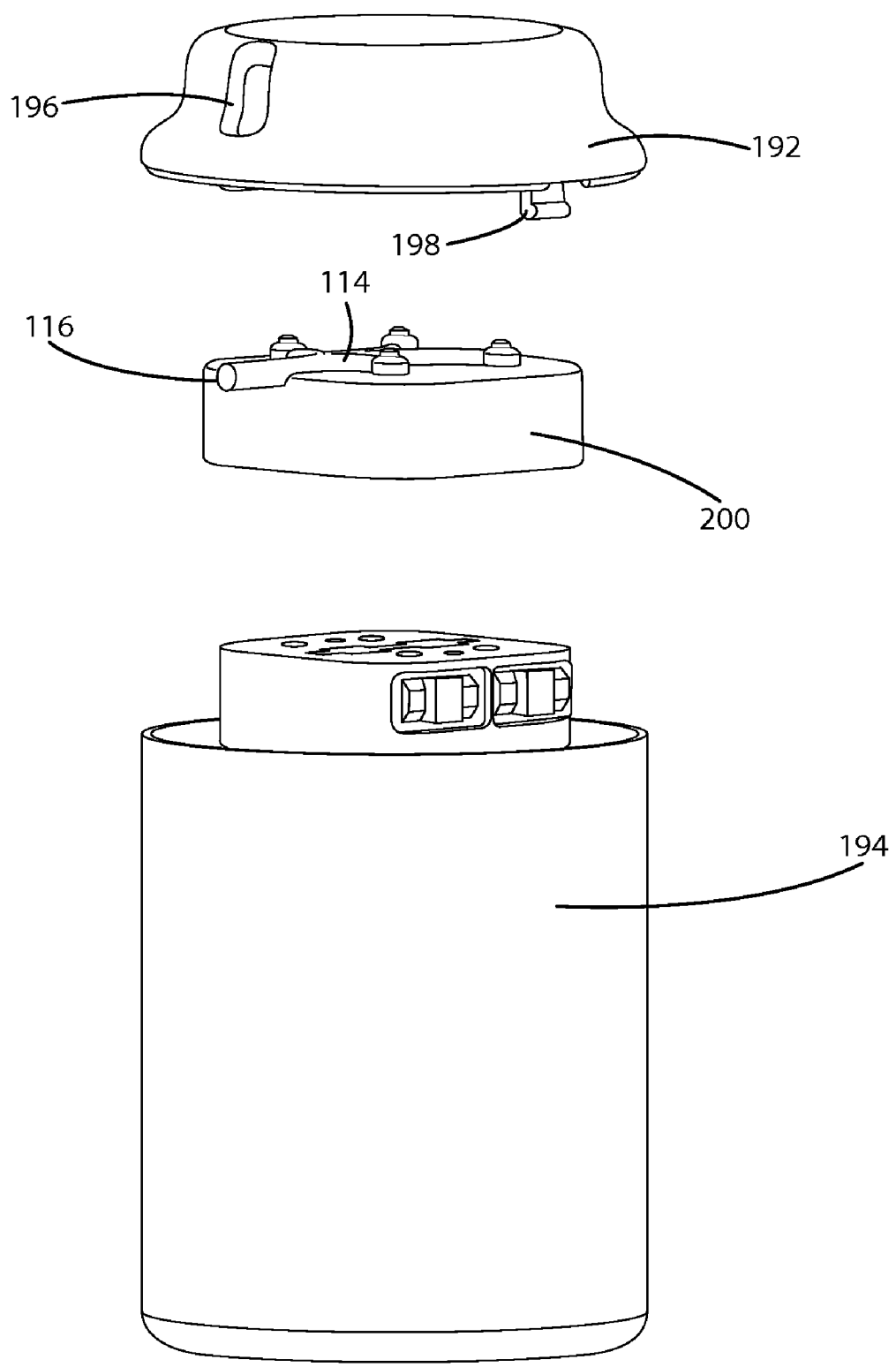
FIG. 13 is an exploded representational perspective view of another embodiment of the present invention.

Multiple valve assemblies 112a-d direct fluid from the pump chamber 94a-d to either a header 114 or the pump chamber 94a-d for recirculation. As shown in FIG. 13, the header 114 is a monolithic manifold in communication with four valve assemblies 112a-d and an exit nozzle 116. While four valve assemblies 112a-d are shown, it will be apparent to those skilled in the art that the number of valve assemblies 112 can vary depending on the desired number of fluid reservoirs 22 in a given application.

Figure 7:
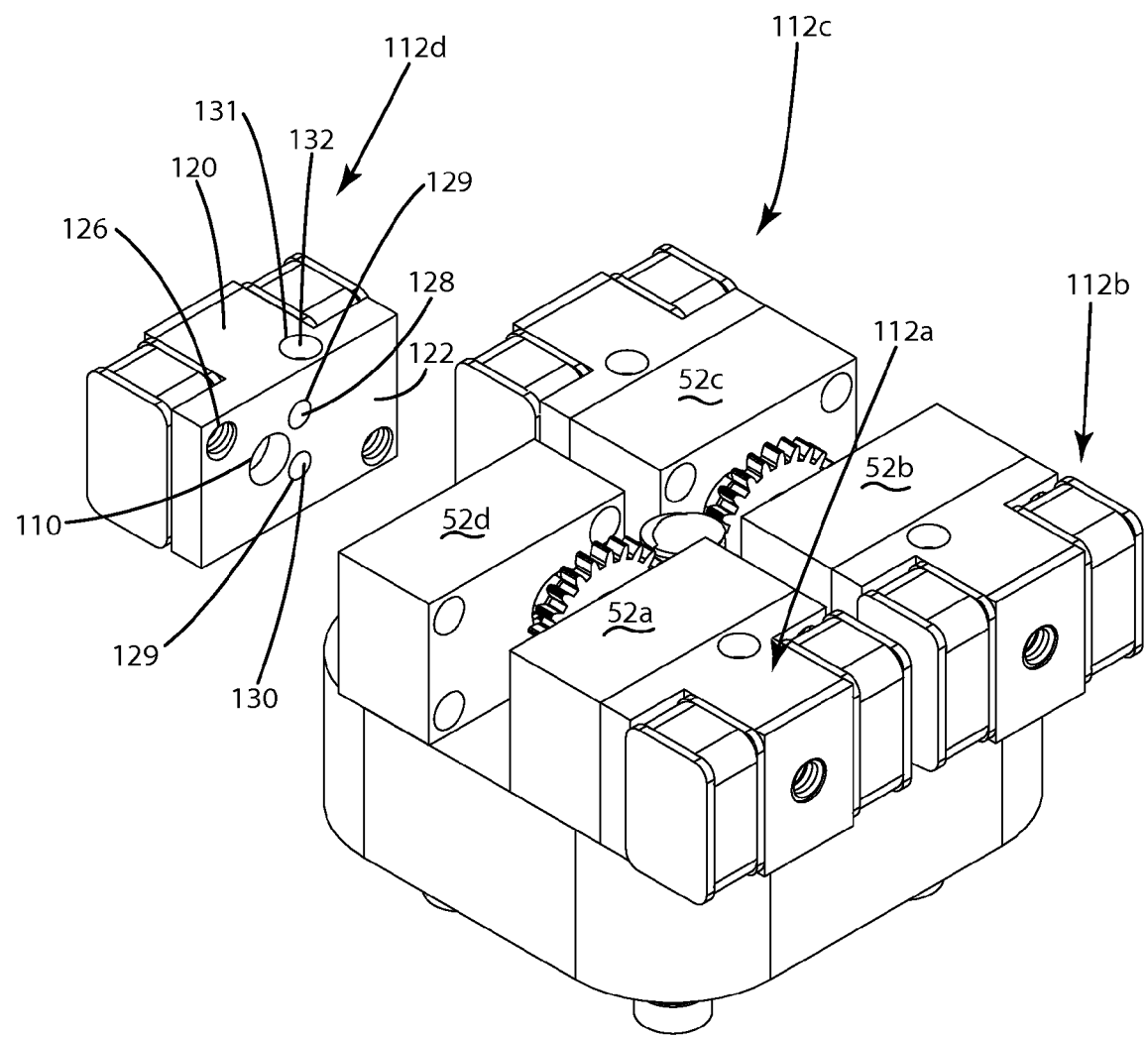
FIG. 7 is a partially exploded representational view of the fluid dispenser of FIG. 2 illustrating the valve assembly.

As more specifically depicted in FIG. 7, each valve assembly 112a-d includes a valve housing 120 including a first surface 122 configured to engage the surface of the pump housing 52 defining the pump chamber 94. The valve housing first surface 122 can include an inlet port 127 connected to an inlet channel 128 and a recirculation port 129 connected to a recirculation channel 130 for fluid communication between the pump chamber 94 and an adjacent valve chamber 134. The valve housing first surface 122 can further include a recess 110 for rotatably supporting the idler shaft 106 and one or more alignment bores 126 to receive cylindrical sleeves 124 from the pump hosing 52.

Figure 8:
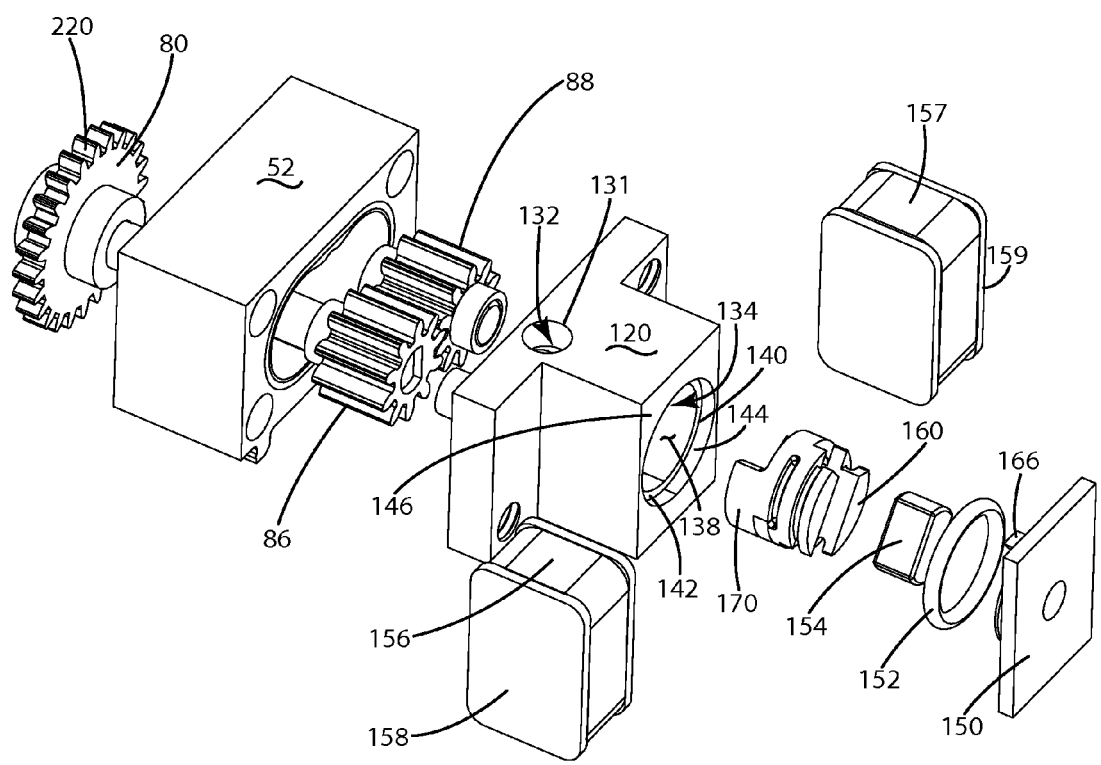
FIG. 8 is a first exploded representational view of the pump and valve assemblies.
Figure 9:
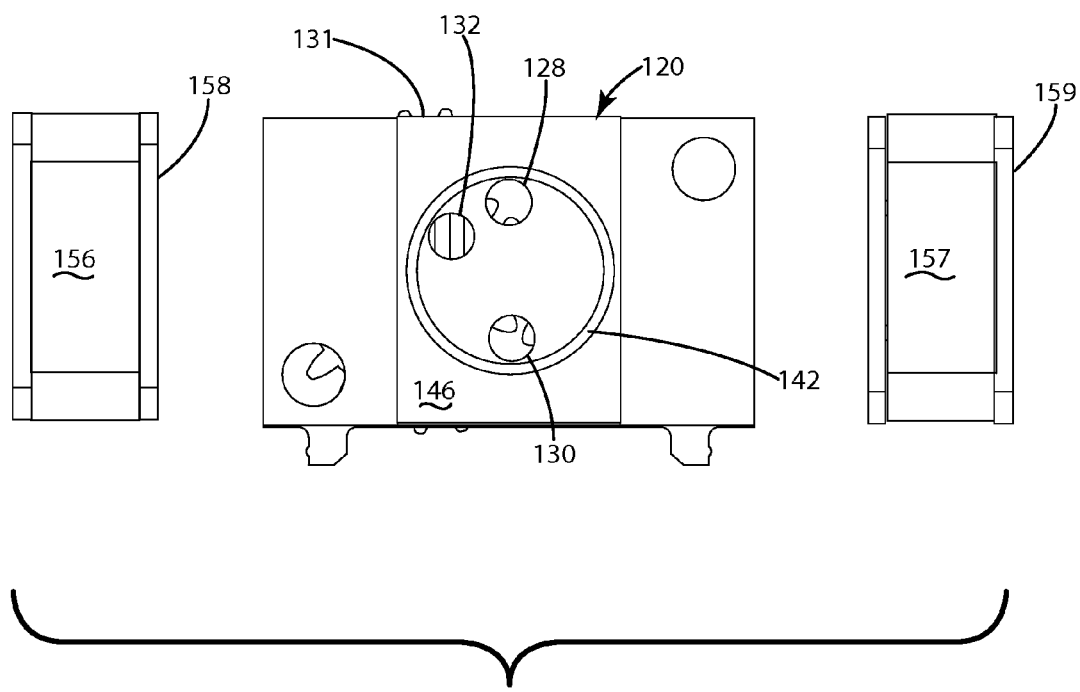
FIG. 9 is a front plan view of the valve assembly and solenoid.
Figure 10:
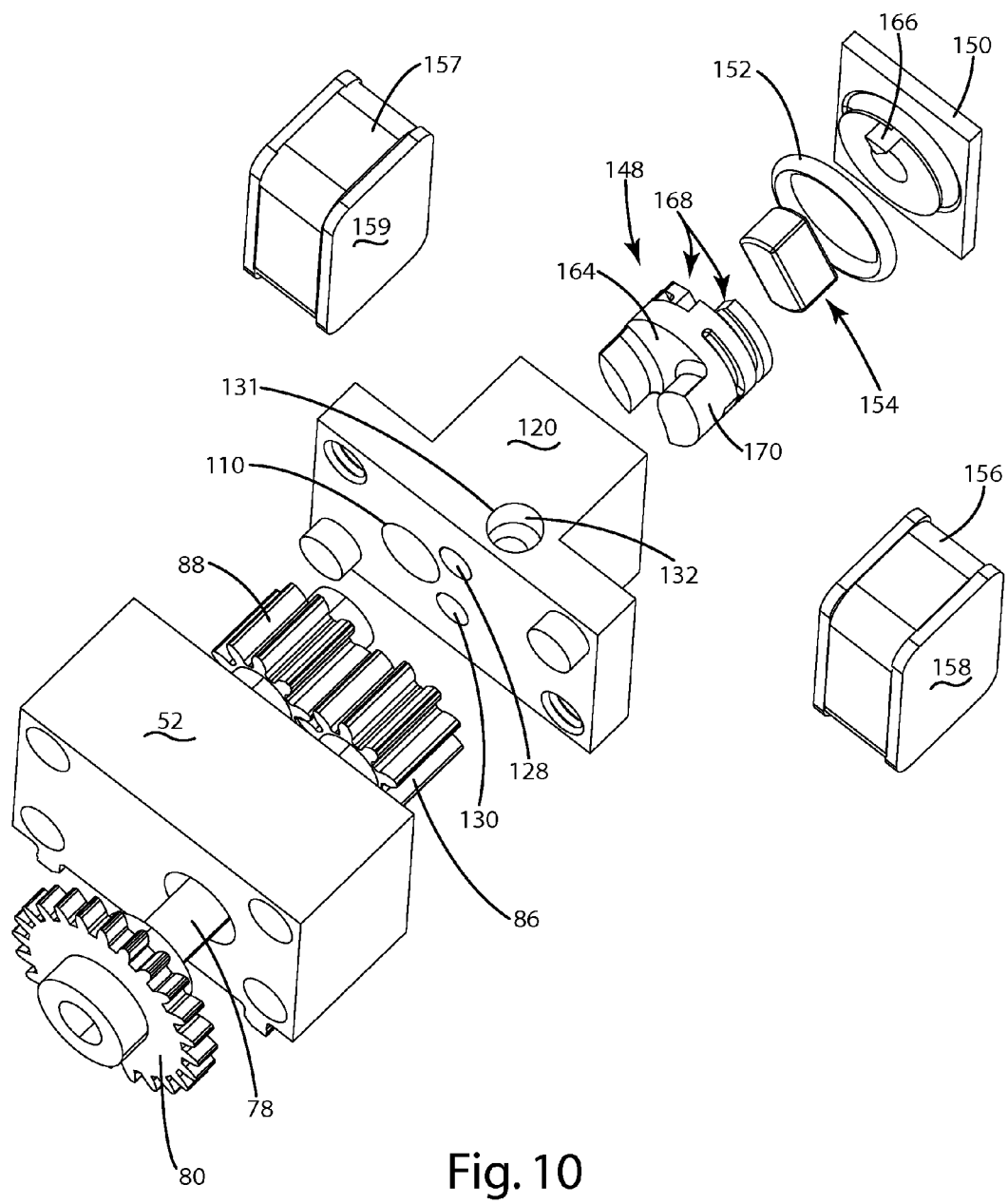
FIG. 10 is a second exploded representational view of the pump and valve assemblies.
Figure 12A:
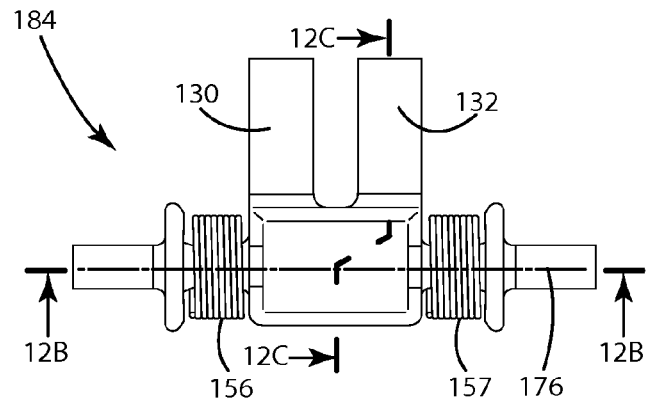
FIG. 12A-D are various illustrations of a flipper valve in accordance with an embodiment of the present invention.
Figure 12B:
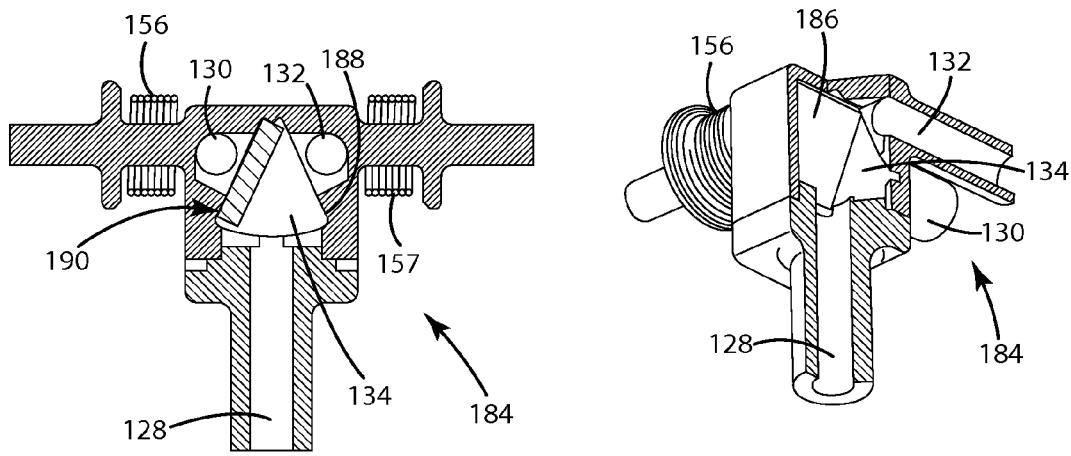
Figure 12C:
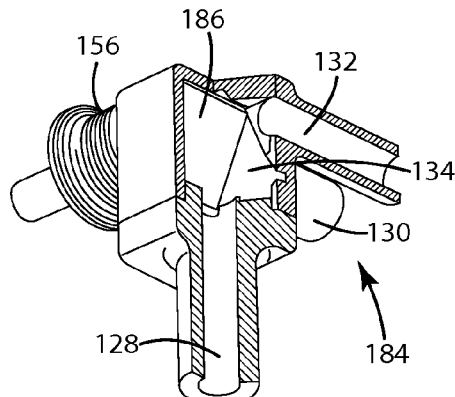
Figure 12D:
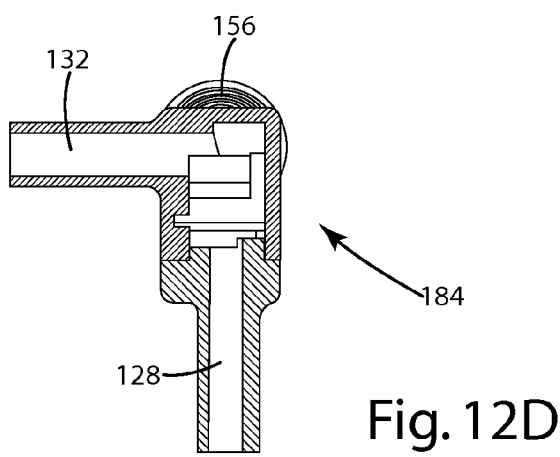

As shown in FIGS. 8-10, each valve chamber 134 can include a generally circular base 136 and a first annular wall 138 extending away from the base 136 and terminating at an annular rim 140. The annular rim 140 can include an outwardly extending ledge 142 with a second annular wall 144 extending from the rim 140 toward a valve housing second surface 146. The valve inlet channel 128 and valve recirculation channel 130 can be disposed between the valve housing first surface 122 and valve chamber base 136. As shown in FIG. 9, the valve inlet channel 128 can be disposed on an exterior portion of the valve chamber base 136 distal from the valve recirculation channel 130. The valve housing 120 can further include an outlet channel 132 connected to an outlet port 131 for fluid communication between the valve chamber 134 and the header 114. The outlet channel 134 can be disposed on a third exterior portion of the valve chamber base 136, wherein the inlet channel 128, recirculation channel 130 and outlet channel 132 are defined by a circular cross section of substantially equal diameter.

In the illustrated embodiment, each valve assembly 112a-d includes a solenoid valve including a rotary valve cylinder 148, valve cap 150, o-ring 152, magnet 154—optionally a bipolar permanent magnet—and two conducting coils 156, 157 and bobbins 158, 159. The valve housing 120 is configured to receive the valve cylinder 148 and permit relative radial movement therebetween. The valve cylinder first surface 160 is configured to fixedly receive the magnet 154, defining a recess 162 of complimentary shape and size to the magnet 154 as depicted in FIG. 8. The valve cylinder 148 includes a second surface 164 opposite the first surface 160 for receiving fluid from the inlet channel 128 and directing the fluids to at least one of the outlet channel 132 and recirculation channel 130.

As shown in FIG. 10, the valve assembly 112 includes a raised stop 166 extending from and integral with the valve cap 150. The valve cylinder 148 includes depressions 168 on the valve cylinder first surface 160 extending from the magnet recess 162 radially outward to the valve cylinder circumferential surface 170. In operation, the stop 166 can interfit between the valve cylinder depressions 168 to limit radial movement of the rotary valve cylinder 148 within the valve housing 120 to less than one hundred and eighty degrees. As also shown, the elastomeric o-ring 152 defines an axial dimension greater than the depth of the annular recess 142 to project outward from the recess 142. Accordingly, the o-ring 152 will be compressed in the recess 142 upon being engaged by the confronting portion of a valve cap 150 to provide a seal between the valve housing 120 and the valve cap 150.

As depicted in FIGS. 8-10, each valve assembly 112 further includes first and second conducting coils 156, 157 wound around the core of first and second bobbins 158, 159 respectively. As shown, the first and second bobbins 158, 159 are seated adjacent opposing portions of the valve housing 120 and define a common longitudinal axis therethrough. In one method of operation, energization of the first coil 156 can produce an attractive force to rotate the valve cylinder 148 within the valve chamber 134 to a first position. Alternatively, de-energization of the first conducting coil 156 and energization of the second conducting coil 157 can produce an attractive force of opposite polarity to rotate the valve cylinder 148 within the valve chamber 134 to a second position. As shown in exploded view in FIG. 10, in the first position the solenoid valve assembly 112 allows recirculation of a fluid. In the second position (not shown) the solenoid valve assembly 112 allows bidirectional movement of a fluid between the pump chamber 94 and the header 114.

In another mode of operation, energization of the first and second conducting coils 156, 157 with a first common polarity can produce an attractive force to rotate the valve cylinder 148 in a first position. Energization of the first and second coils 156, 157 with a second polarity can produce an attractive force to rotate the valve cylinder 148 in the second position. Additionally, the valve assembly 112 can include a biasing mechanism (not shown) to bias the valve cylinder 148 in the first position when the dispenser 20 is not in use, thereby preventing the unwanted outlet of fluid into the header 114.

In another embodiment, the dispenser 20 may include valve assembly 112 including a gate valve 174. As show in FIGS. 11A-C, opposing solenoid coils 156, 157 define a common longitudinal axis 176 for actuating a rectangular magnetic gate plate 178 within a valve seat 180. In the closed position, the gate plate 178 overlays the outlet channel 132. The gate plate 178 may be magnetically polarized traverse to its longitudinal axis in a direction parallel to the valve seat 180. In operation, one or more solenoid coils 156, 157 are energized by the dispenser power supply 182, producing a magnetic field to slideably urge the gate plate 174 to the open position. In the open position, the inlet channel 128 is in open communication with the outlet channel 132. To return to the closed position, the solenoid coils 156, 157 are energized with an opposite current to produce a magnetic field of opposite polarity, thereby urging the gate plate 178 to the closed position for recirculating the fluid to the fluid reservoir 31 via the pump housing 52. Alternatively, the gate valve 174 is biased in the closed position by a spring or other biasing mechanism (not shown). From the open position, the biasing mechanism may return the gate plate 178 to the closed position as the solenoid coils 156, 157 are de-energized.

In still another embodiment, the dispenser 20 may include a valve assembly 112 including a flipper valve 184. As shown in FIGS. 12A-D, opposing solenoid coils 156, 157 define a common longitudinal axis 176 for actuating a rectangular magnetic flip plate 186 within a valve chamber 134. In the closed position, the flip plate 186 is mechanically or electromagnetically biased toward a first portion 188 of the valve chamber 134, thereby sealing the outlet channel 132 from the inlet channel 128. In operation, one or more solenoid coils 156, 157 are energized by the dispenser power supply 182, producing a magnetic field to pivot or 'flip' the flip plate 186 toward a second portion 190 of the valve chamber 134. In this open position, depicted in FIGS. 12A-D, the recirculation channel 130 is sealed from the inlet channel 128, and the inlet channel 128 is in fluid communication with the outlet channel 132. To return to the closed position, the solenoid coils 156, 157 are energized with an opposite current to produce a magnetic field of opposite polarity, thereby urging the flipper valve 184 to the closed position for recirculating the fluid to the fluid reservoir 31 via the pump housing 52. Alternatively, the flip plate 186 is biased in the closed position by a spring or other biasing mechanism (not shown) without the aid of a magnetic field. From the open position, the biasing mechanism may return the flip plate 186 toward the first portion 188 of the valve chamber 134 as the solenoid coils 156, 157 are de-energized.

As further depicted in FIG. 13, the dispenser 20 exterior may include a cap 192 configured to engage a base 194 for forming an enclosure. The cap 192 as shown includes a nozzle port 196 and a flexible barbed connector 198 for securing the cap 192 to the base 194. The header 114 is joined to an intermediate cover 200 for shrouding the pump housings 52a-d, valve assemblies 112a-d and manifold 28. When the cap 192 is joined to the base 194, the header nozzle 116 extends through the nozzle port 196 to allow for convenient application of the fluid as desired by the user. Optionally, the dispenser 20 can include a foaming or atomizing means (not shown) for achieving a desired consistency for a given application.

As depicted in FIG. 1B, the dispenser control system 30 includes a power supply 182, optionally including a rechargeable battery. The power supply 182 is coupled to a recharging means, for example conventional leads for charging within a contact base. In the illustrated embodiment, the dispenser 20 is configured to be inductively coupled to an inductive power supply for recharging the dispenser power supply 182. FIG. 1B shows a cross sectional view of the dispenser of FIG. 1A. An inductive charging secondary coil 204 circumferentiates an interior portion 206 of the base 194 for inductively coupling to an inductive primary (not shown). The associated inductive primary may be coupled with essentially any inductive power supply circuitry, but, in the illustrated embodiment, includes eCoupled™ inductive power supply circuitry available from Fulton Innovation of Ada, Mich. Additionally, the dispenser power supply 182 may be capable of transmitting data communications with outside devices, for example, to communicate status, composition formulations and other information. The communications may be carried over the primary and secondary coil, for example, using backscatter modulation with differential biphase encoding. Alternatively, the system may include a separate communications link for communications, such as a Bluetooth™, RFID, WiFi, infrared (IR), Near Field Communications, or other wireless communications link.

The power supply 182, valve assemblies 112, motor 26 and selectable user interface 208 are electronically coupled to the dispenser control system 30, optionally a microprocessor control means 212 and memory 213. In operation, the control system 30 regulates the quantity and composition of the dispensed fluid according to user-supplied data or a pre-set formula. Exemplary cosmetic formulas are disclosed in U.S. Pat. No. 6,986,442 to Engel et al and U.S. Pat. No. 6,715,642 to Engel et al, which are hereby incorporated by reference in their entirety. On command from the control system 30, the motor 26 operates in a given direction and power setting or speed, drawing power from the dispenser power supply 182. As described in more detail above, the motor 26 provides a motive force for the pumps 24a-d via a single transmission 74. In the illustrated embodiment, each of four pump housings 54a-d include identical gear pumps 86a-d, 88a-d. However, the dispenser 20 may include gear pumps having non-identical gear ratios to achieve non-identical flow rates as desired. The control system 30 further controls the flow of each of four fluids through corresponding valve assemblies 112a-d. To achieve a desired composition, the control system 208 actuates each valve 170a-d between the recirculation channel 130 and the outlet channel 132. Positive pressure from the pump chambers 94 motivates the fluids through the valve assemblies 112a-d while metered by the control system 30. The outlet channel 132 routes a fluid to the header 114 when desired in the dispensed composition, and the recirculation channel 130 returns fluid to the fluid reservoir 32 when that particular fluid is not desired, thereby creating a dispensed composition having the required proportion of constituent fluids. When the desired quantity of dispensed composition is achieved, the control system 30 returns each valve 170a-d to a closed or re-circulate position and stops operation of the motor 26.

To aid in the actuation of one or more valves 170a-d, for example when the desired composition includes a viscous constituent fluid, the control system 30 can interrupt the operation of the motor 26 during a dispensing routine, manipulating motor direction and/or speed to relieve pressure on one or more valves 170a-d. For example, the control system 30 can reduce the motor speed, de-activate the motor, reverse the motor 26 direction, or any combination of the above. After actuation of one or more valves 170a-d, the control system 30 can then re-activate the motor 26 to a desired speed and direction, optionally returning to pre-interruption values. Additionally, to aid in the actuation of one or more valves 170a-d, the control system 30 can initiate a dispensing routine from rest by first activating the motor 26 in a reverse direction, opposite the direction corresponding to normal fluid flow. After a predetermined time, the control system 30 can activate the motor 26 in a forward direction and begin the dispensing process as discussed above.

At the completion of a dispensing routine, the header 114 or one or more valve assemblies 112a-d can contain residual amounts of constituent fluid. If allowed to remain in the header 114 or one or more valve assemblies 112a-d, a constituent fluid can coagulate, oxidize, become contaminated, mix with another constituent fluid, or otherwise become undesirable as a constituent fluid. For at least these reasons, at the completion of a dispensing routine the control system 30 can activate the motor 26 in the reverse direction to draw fluid toward the pump assemblies 24a-d, and ultimately to the fluid reservoirs 32a-d. The dispenser 20 may also include one or more one-way check valves (not shown) to prevent backflow of a composition comprising one or more constituent fluids. One or more check valves can be positioned in the outlet channel 132, header 114, cover 200 or valve assemblies 112a-d, oriented to allow fluid to pass in a direction toward the exit nozzle 116. In one embodiment, the dispenser 20 includes four flexible rubber duckbill valves, located in separate flow paths within the header 114 and upstream of the convergence of any two or more flow paths. In another embodiment, the dispenser 20 includes four check valves, each located in an outlet channel 132 within a respective valve assembly 112a-d. In still another embodiment, the dispenser includes a single check-valve located in the header 114 downstream of the convergence of two or more flow paths, optionally at the exit nozzle 116.

In one embodiment, metering is achieved by measuring the time intervals for actuation of the valve assembly 112. For more viscous fluids, the control system 30 can increase the time interval for actuation of a given valve assembly 112 and increase the motor speed. For less viscous fluids, the control system 30 can decrease the time interval for actuation of a given valve assembly 112 and decrease the motor speed. Optionally, a valve assembly 112 can cycle during use for grossly mixing a fluid into a desired composition. For example, it may be desired to combine two fluids, such as a solute and a solvent, in dramatically different proportions. To accomplish a dispensed fluid of more uniform composition, the control system 30 can cycle a first valve assembly 112a between 'discharge' and 'recirculate' in uniform intervals $T_1$ for administering a solute, while a second valve assembly 112b remains in the 'discharge' or open configuration for a period $T_2$ for administering the solvent, where $T_1<T_2$. The period $T_1$ may be selected so that the solute (which is smaller in volume) is intermittently, but uniformly, added to the solvent (which is greater in volume) over the full discharge period. Accordingly, by grossly mixing constituent fluids, the dispensed composition is relatively uniform even though containing a solute in small proportions to the solvent. Generally, if it is desirable to mix two constituents in a roughly 2 to 1 proportion, the control system may run the motor for the time period required to discharge the more prominent constituent. During this period of time, the valve for the less prominent constituent can be turned off and on in even intervals to distribute the less prominent constituent more evenly throughout the more prominent constituent. The cycle time (i.e. the amount of time the valve is 'off' and 'on') of the valve controlling the flow of the less prominent constituent can be selected to mix constituent of essentially any proportions. This method of operation can be adapted for multiple fluid constituents as desired, for example, by properly cycling the valves for all of the constituents except the constituent of the greatest volume.

In another embodiment, metering is achieved with a transducer 214, for example an LED 214 and photosensor 216 adapted to identify radial movement of a drive gear 80. As illustrated in FIG. 2, the LED 214 and photosensor 216 are oriented such that the light from the LED 214 passes between drive gear teeth toward 220 the photosensor 216 during operation of the drive gear 80. Each pulse of light received by the photosensor 216 is communicated to the control system 30 as radial movement of the drive gear 80. In another embodiment, the LED 214 and photosensor 216 can be oriented such that light from the LED 214 is reflected off passing gear teeth 220 and onto the photosensor 216. Each pulse of reflected light can be communicated to the control system 30 as radial movement of the drive gear 80.

The dispenser 20 as shown also includes a selectable user interface 208, optionally a portion of the base 194 and including a display 222 and user selection buttons 224. The display 222 may indicate a power value, such as battery level or charging status. Additionally, the display 222 may indicate a series of selectable compositions, composition histories or fluid reservoir levels.

A fluid dispenser 20, optionally including the features as aforementioned, may be configured to generate a variety of dispensed compositions in accordance with any number of formulas. Generally, the fluid dispenser 20 may include a control system 30 containing one or more pre-programmed formulas for a given range of constituent fluids. Optionally, the fluid dispenser 20 selectable user interface 208 can enable a user to select from the available pre-programmed formulas. The selectable user interface 208 can also enable a user to customize or even create formulas as desired, such as by accepting user-supplied preferences and known allergic conditions. Additionally, the control system 30 can be configured to create a regimen of dispensed compositions, including a plurality of compositions containing varying proportions of constituent fluids over time. The regimen may be a preprogrammed series of formulas, optionally variable according to user-supplied preferences and other data, or may be supplied by a user or third party via the selectable user interface 208 or other method of communication.

Figure 14:
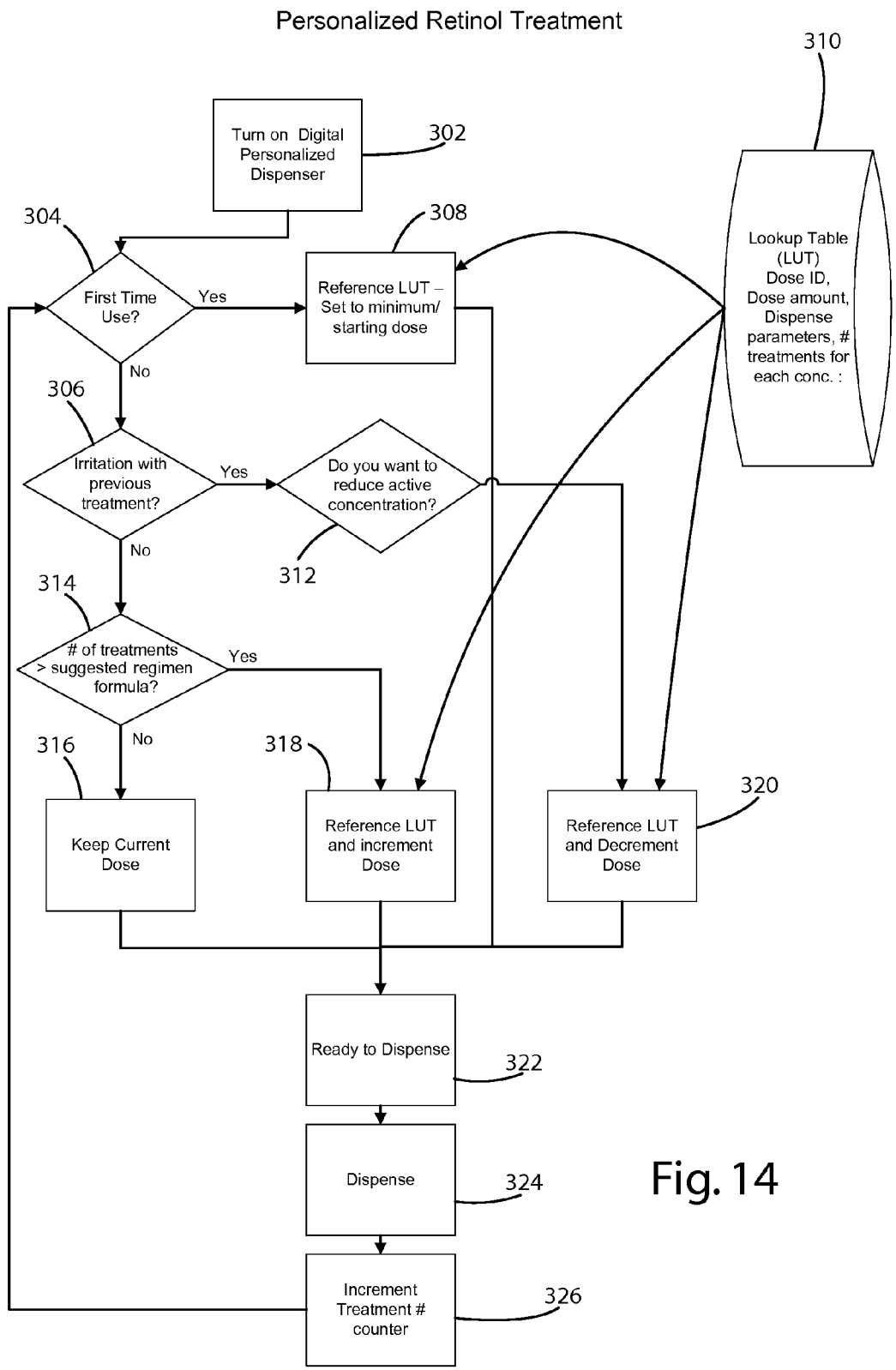
FIG. 14 is a flowchart showing the general steps of a method of operation for personalizing a retinol treatment in accordance with an embodiment of the present invention.

One method of operation is depicted in FIG. 14 in connection with the production of a personalized retinol treatment regimen. In this embodiment, a user is guided through a series of user input prompts 304, 306, 312 by the dispenser selectable user interface 208. As described in more detail below, user input may be solicited before the regimen begins and/or between treatments to affect the formulations blended and dispensed during the regimen. Upon activating 302 the dispenser, a user can select whether the present use of a retinol treatment is a first time use at user input prompt 304. Although the question in this embodiment is intended to assess whether this is the first treatment in a regimen of treatment, in other applications the question may be directed to whether or not the user has previously gone through the treatment regimen. In still other applications, this question may be altogether eliminated. Returning to the embodiment of FIG. 14, the user may select 'yes' or 'no' using the user selection buttons 224 on the selectable user interface 208. If the user selects 'yes,' indicating that this will be the first retinol treatment for this regimen, the control system 30 will select 308 a formula containing a starting dose of retinol with reference to a Look Up Table 310 stored in a control system memory 213. The information contained in the Look Up Table 310 may vary from application to application. For example, the Look Up Table 310 may include formulas or other data that will allow the system to calculate or otherwise generate the formulas for the different treatments in the regimen. As another example, the Look Up Table 310 may include the specific volumes or proportions of each of the constituent fluids for each treatment in the regimen. If the user instead selects 'no,' indicating a prior treatment in the retinol regimen, the user is guided through a different series of user input prompts 306, 312 directed towards providing a treatment in accordance with the treatment regimen and modified as needed. These and other input prompts may be used to allow some customization of the regimen, for example, to reduce the strength of the treatments if the user experiences irritation or increase the strength of the treatments if appropriate. In other applications, the user may be able to customize other aspects of the treatments, for example, by varying base, fragrances or other constituent components. In some applications, the active ingredient(s) must be increased according to a schedule to reduce the risk that the user will have an adverse reaction to the treatment. For example, in some applications, it may be necessary for an active ingredient to be applied a specified number of days to allow the user's skin to adjust before it receives an increased dose. This information may be stored in the Look Up Table 310. In this particular application, the system provides the ability for the user to reduce the amount of the active ingredient if skin irritation occurs. At user input prompt 306, a user is asked if he or she experienced irritation with the prior treatment formula. If the user selects 'no,' the dispenser control system 30 determines 314 whether it is appropriate to increase the dose of the active ingredient(s). In this application, the dispenser 20 determines whether it has issued the suggested number of treatments for a given regiment formula (e.g., seven treatments at 0.5% retinol). To facilitate this function, the history of dispensed treatments may be stored as described in more detail below. Depending on the result, the control system 30 will maintain 316 the current dose of retinol or may reference the Look Up Table 310 to determine the appropriate increase 318 in the dose of retinol. If at user input prompt 306 the user had indicated irritation with prior treatments, the user at prompt 312 can indicate a desire to reduce the dose of a constituent fluid—retinol in the current example. The control system 30 can then provide 320 a formula having a decreased dosage of retinol, optionally through reference to the Look Up Table 310.

At this stage, the desired treatment is ready to dispense 322 and dispensed 324, optionally at the command of the user. The dispenser may store 326 in a memory 213 data representative of the history of dispensed treatments, such as the formula of the delivered treatment, the date/time of delivery and other associated data. The data collection function 326 can include storing 1) the number of treatments yet provided in a given regimen, 2) when the treatments were dispensed, 3) what the treatments were comprised of, 4) which treatments included a user-requested decrease in active ingredient, and 5) which treatments were pursuant to an indicated irritation to a previous treatment. Additionally, the control system 30 can reference from memory 213 the prior formula of the delivered treatment for subsequent iterations of the illustrated method. In an alternative embodiment, user input prompt 304 is instead a control system decision operation, or is a combination of user input and control system decision operation. For example, with reference to the memory 213, the control system 30 can determine 304 whether the use of the dispenser 20 is a first time use for a retinol treatment regimen without a user input by referencing the history of applied treatments stored in memory.

As noted above, the information stored in the Look Up Table 310 may vary from application to application depending in large part on what information is needed to allow the control system to provide the desired functionality. In the aforementioned method, the Look Up Table 310 can contain Dose ID/Treatment No. (e.g., treatment No. 1 of a 28 day treatment regimen), Dose Amount (e.g., 5% retinol), Dispense Parameters (e.g., bases and other constituents and corresponding proportions, motor run times, valve actuation profiles), and number of treatments at a given concentration (e.g., seven treatments at 0.5% retinol). Additionally, the selectable user interface 208 can provide reservoir placement instructions to the user for ensuring each fluid reservoir 32a-d contains the correct constituent fluid. Alternatively, the dispenser control system 30 can accept user-supplied data indicating reservoir content, optionally utilizing less than the maximum available reservoirs as desired in a given application. For example, the selectable user interface 208 can receive a series of inputs indicating the first reservoir 32a includes retinol, the second reservoir 32b includes a moisturizer, and the third reservoir 32c includes a base for distributing the retinol and moisturizer.

In another method of operation as depicted in FIG. 15, a user desirous of a customized anti-aging treatment regimen is guided through a series of user input prompts 342, 344, 346, 360 by the dispenser selectable user interface 208. Upon activating 302 the dispenser, a user can select whether the present use of an anti-aging treatment is a first time use at prompt 342. If the user selects 'yes,' indicating a first time use, the control system 30 will select 350 a starting formula with reference a Look Up Table 348. The user will again be prompted 344, allowing a user to indicate known allergies to fragrances or other constituents present in the starting formula. If the user indicates known allergies to a fragrance present in the starting formula, the control system 30 will remove 352 all or a portion of the fragrance from the formula. The control system will then display 354 the current formula for further modification or dispensing as explained below.

If the user had instead indicated a prior use of anti-aging treatment when prompted 342, the control system will display 356 the previous treatment formula. The user will again be prompted 346, allowing a user to indicate irritation with prior treatments. If the user selects 'yes,' indicating prior irritation, the control system 30 will remove 358 at least a portion of anti-aging active from the formula and display 354 the current formula. If the user selects 'no,' the control system 30 will merely display 354 the current formula.

After the control system displays 354 the current formula, the user is again prompted 360, and the user may indicate whether the displayed formula is acceptable. If the user selects 'no,' the control system 30 will modify 362 the formula with reference to the Look Up Table 348, memory 213, user inputs or any combination of the same. A user will again be prompted 360 with whether the modified formula is acceptable. Here too, the control system 30 will modify 362 the formula if desired, or make ready 364 for dispensing the selected formula. Optionally, the control system 30 can limit modification 362 of a formula to ensure the formula is not outside acceptable parameters or suggested user conditions. Finally, the desired anti-aging treatment is dispensed 366, optionally at the command of a user, and the dispenser 20 stores 368 the delivered treatment and associated data in memory 213.

The data collection function 368 can also include storing 1) the number of anti-aging treatments yet provided, 2) when the treatments were dispensed, 3) what the treatments were comprised of, 4) which treatments were pursuant to an indicated prior irritation at prompt 346, and 5) which treatments were pursuant to an indicated allergic condition at prompt 344. The Look Up Table 348 can contain Dose ID/Treatment No. (e.g., treatment No. 14), Dose Amount (e.g., 0.5% anti-aging active), Dispense Parameters (e.g., bases and other constituents and corresponding proportions, motor run times, valve actuation profiles), and number of treatments at a given concentration (e.g., seven treatments at 0.5% anti-aging active) for a given anti-aging treatment regimen.

Additionally, in subsequent iterations of the illustrated method, the control system 30 can reference from memory 213 or the Look Up Table 348 one or more prior treatment formulas. For example, the user input prompt 342 is instead a control system decision operation. With reference to the memory 213, the control system 30 can determine 342 whether the use of the dispenser 20 is a first time use of an anti-aging treatment regimen. The dispenser can then display 356 the previous treatment formula (if any) with reference to the memory 213 or Look Up Table 348.

In the present example, the customized anti-aging treatment utilizes one reservoir 32a for containing anti-aging active, two reservoirs 32b-c for containing fragrances, and one reservoir 32d for containing a base. The selectable user interface 208 can provide reservoir placement instructions to the user for ensuring each fluid reservoir 32a-d is in fluid communication with the appropriate pump 24a-d and valve assembly 112a-d. Alternatively, the dispenser control system 30 can accept user-supplied data indicating reservoir content, optionally utilizing less than the maximum available reservoirs as desired in a given application.

It is envisioned that the present invention is adapted to be connected to a stand-alone or remote computer. Formula information may be stored in the computer's hardware, software, or a website set up for the dispenser 20. The dispenser 20 may include a plug-in for hooking the computer up to the dispenser 20, such as a USB port, serial port, parallel port or other communications port. Alternatively, the dispenser 20 may include a capability for wireless communication with the stand-alone or remote computer, optionally over a network, such a Bluetooth™, RFID, WiFi, IR, Near Field Communications or other wireless communications link. In this way, a wireless transceiver could eliminate the need for a communications port and enhance the dispenser's 20 portability. In one operation, a user might choose a shade for a cosmetic using the computer, which would download the particular formula into the dispenser control system 30 for immediate dispensing of the desired shade. The computer may include a database of pre-created formulas or may create the formula in real time through user interaction. The computer may also permit the user to enter a formula. Additionally, the dispenser 20 may communicate a model or serial number, usage profile, and fluid reservoir status to a network, optionally via the computer to a web-site set up for the dispenser 20, for generating product recommendations. The web site can further permit ordering and reordering of parts, accessories and consumable materials based on data provided by the dispenser 20 or user. In one embodiment, the dispenser can communicates fluid reservoir information, such as fluid reservoir status or a reorder request, to a remote computer for ordering a replacement fluid or fluid reservoir when the constituent fluid in a fluid reservoir falls below a predetermined volume.

The above description is that of the current embodiment of the invention. Various alterations and changes can be made without departing from the spirit and broader aspects of the invention as defined in the appended claims, which are to be interpreted in accordance with the principles of patent law including the doctrine of equivalents. Any reference to elements in the singular, for example, using the articles "a," "an," "the," or "said," is not to be construed as limiting the element to the singular.

The embodiments of the invention in which an exclusive property or privilege is claimed are defined as follows:

1. A handheld fluid dispensing system comprising:
   a first and second fluid reservoir configured to contain a first and second constituent, respectively;
   a first and second pump, said first and second pump in communication with said first and second fluid reservoir, respectively;
   a drive motor, said first and second pump commonly driven by said drive motor;
   a control system, said control system coupled to said drive motor;
   a first and second valve assembly, said first and second valve assembly in communication with said first and second pump, respectively, each of said first and second valve assemblies including a valve chamber in communication with an inlet port via an inlet channel, an outlet port via an outlet channel, and a recirculation port via a recirculation channel;
   a first and second moving valve member disposed in said first and second valve chamber, respectively, and responsive to said control system for directing a constituent between said inlet channel and one of said outlet and recirculation channels, wherein said control system selectively actuates said first and second moving valve members for dispensing a composition containing desired proportions of said first and second constituents; and
   a handheld enclosure, wherein said first and second fluid reservoirs, said first and second pumps, said drive motor, said control system, said first and second valve assemblies and said first and second moving valve members are supportably received within said handheld enclosure.

2. The fluid dispenser of claim 1, wherein said control system is adapted to dispense a plurality of compositions in accordance with a predetermined regimen having varying proportions of said first and second constituents.

3. The fluid dispensing system of claim 1, wherein said first moving valve member includes at least one of a rotary valve, gate valve and flipper valve.

4. The fluid dispenser of claim 1, further including a header in fluid communication with said first and second valve assembly outlet ports.

5. The fluid dispenser of claim 1, wherein said control system includes a microprocessor, said microprocessor programmable by at least one user for selecting a desired dispensed composition.

6. The fluid dispenser of claim 1, further comprising a computer plug-in for receiving customized formulas from a remote computer.

7. The fluid dispenser of claim 1, further comprising a rechargeable power supply and inductor configured to receive AC electrical power from an external inductive power supply.

8. The fluid dispenser of claim 1, further comprising a transducer coupled to said control system and including a photosensor and LED for metering at least one of said first and second pump assemblies.

9. A handheld fluid dispensing system comprising:
   a drive motor;

a header;

a plurality of fluid reservoirs;

a plurality of pump assemblies commonly driven by said drive motor, wherein a first and a second of said pump assemblies are in communication with a first and a second of said fluid reservoirs, respectively;

a plurality of valve assemblies each including an inlet channel in communication with a first portion of one of said pump assemblies, outlet channel in communication with said header, recirculation channel in communication with a second portion of said one of said pump assemblies, and including a magnetic moving member for directing fluid from said input channel to one of said output channel and said recirculation channel;

a control system coupled to said drive motor and said first and second valve assemblies, wherein said control system activates said drive motor and said first and second valve assemblies in accordance with a formulation to generate a fluid composition; and a handheld enclosure, wherein said drive motor, said plurality of fluid reservoirs, said plurality of pump assemblies, said plurality of valve assemblies and said control system are supportably received within said handheld enclosure.

10. The dispenser of claim 9, wherein said control system includes a memory for storing a plurality of formulations.

11. The dispenser of claim 9, wherein said control system includes a microprocessor, said microprocessor programmable by at least one user for selecting at least one of said plurality of formulations.

12. The dispenser of claim 9 further comprising a computer plug-in for receiving customized formulations from a remote computer.

13. The dispenser of claim 9 wherein said magnetic moving member includes at least one of a rotary valve, gate valve and flipper valve.

14. The dispenser of claim 9 further comprising a rechargeable power supply and inductor configured to receive AC electrical power from an external inductive power supply.

15. The dispenser of claim 9 further comprising a transducer coupled to said control system and including a photosensor and LED for metering said pump assembly.

16. A method of providing a regimen of customized fluid, the regimen including a plurality of compositions to be dispensed over time, comprising the steps of:

providing a handheld fluid dispenser including a control system, a plurality of fluid reservoirs containing constituent fluids, a drive motor, and a plurality of valve assemblies;

providing a regimen defining a plurality of composition formulas to define the plurality of compositions to be dispensed over time, the plurality of composition formulas including varying proportions of one or more of the constituent fluids; and activating the drive motor and valve assemblies with the control system to dispense the plurality of compositions from the fluid reservoirs over time in accordance with the regimen.

17. The method of claim 16, further comprising the step of receiving a regimen from a remote computer.

18. The method of claim 16, furthering comprising the step of receiving user-supplied data for formulating a regimen.

19. The method of claim 16, further comprising the step of communicating fluid reservoir information to a remote computer for ordering a fluid reservoir containing a desired constituent fluid in response to at least one of the plurality of fluid reservoirs achieving a fluid volume below a predetermined value.

20. The method of claim 16, further comprising the step of communicating fluid reservoir information to a remote computer for ordering a desired fluid in response to at least one of the plurality of fluid reservoirs achieving a fluid volume below a predetermined value.

21. A method of providing a customized fluid, comprising the steps of:

providing a handheld fluid dispenser including a drive motor, a control system, a plurality of valve assemblies, a plurality of fluid reservoirs each containing a constituent, and a handheld enclosure;

generating a flow of a first constituent from a first of the fluid reservoirs;

generating a flow of a second constituent from a second of the fluid reservoirs;

directing the flow of a first constituent to a first of the valve assemblies, the first of the valve assemblies configured to selectively discharge or recirculate the flow of a first constituent; and directing the flow of a second constituent to a second of the valve assemblies, the second of the valve assemblies configured to selectively discharge or recirculate the flow of a second constituent;

wherein the first and second of the valve assemblies are responsive to the control system for dispensing a fluid containing desired proportions of the first and second constituents.

22. The method of claim 21, further comprising the step of providing a means for metering the flow of at least one of the first constituent and the second constituent.

23. The method of claim 22, wherein said step of providing a means for metering the flow of at least one of the first constituent and the second constituent further includes the steps of:

providing an LED, photosensor, drive gear, and drive gear teeth;

positioning the drive gear between the opposing LED and the photosensor;

directing light from the LED between adjacent drive gear teeth to the photosensor;

detecting light from the LED with the photosensor for determining radial movement of the drive gear.

24. The method of claim 21, further comprising the steps of:

actuating a first of the valve assemblies for discharge of a first constituent for a first period;

actuating a second of the valve assemblies for intermittent discharge of a second constituent for a second period and during the discharge of a first constituent;

wherein the first period is greater than the second period for grossly mixing the first and the second constituent fluids.

* * * * *